(12) United States Patent
Itai

(10) Patent No.: US 9,968,278 B2
(45) Date of Patent: May 15, 2018

(54) MEDICAL IMAGE MEASURING APPARATUS, METHOD, AND MEDIUM

(71) Applicant: FUJIFILM Corporation, Minato-ku, Tokyo (JP)

(72) Inventor: Yoshinori Itai, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 153 days.

(21) Appl. No.: 14/820,623

(22) Filed: Aug. 7, 2015

(65) Prior Publication Data

US 2016/0063700 A1 Mar. 3, 2016

(30) Foreign Application Priority Data

Sep. 1, 2014 (JP) ................................ 2014-176911

(51) Int. Cl.
*G06K 9/00* (2006.01)
*A61B 5/055* (2006.01)
(Continued)

(52) U.S. Cl.
CPC ............ *A61B 5/055* (2013.01); *A61B 5/1075* (2013.01); *G06T 7/0012* (2013.01); *A61B 5/743* (2013.01); *A61B 6/032* (2013.01); *A61B 6/468* (2013.01); *G01R 33/5608* (2013.01); *G06F 19/321* (2013.01); *G06T 2207/10072* (2013.01); *G06T 2207/30096* (2013.01); *G06T 2210/41* (2013.01)

(58) Field of Classification Search
CPC ....... A61B 5/055; A61B 5/1075; A61B 5/743; A61B 6/032; A61B 6/468; G06T 7/0012; G06T 2207/10072; G06T 2207/30096; G06T 2210/41; G01R 33/5608; G06F 19/321

See application file for complete search history.

(56) References Cited

U.S. PATENT DOCUMENTS 7,092,748 B2 * 8/2006 Valdes Sosa ............ A61B 5/04
600/407
8,099,299 B2 * 1/2012 Sirohey ................. G06F 19/321
348/47

(Continued)

FOREIGN PATENT DOCUMENTS

JP 9-251364 A 9/1997
JP 2000-185038 A 7/2000
(Continued)

OTHER PUBLICATIONS

Communication dated Nov. 8, 2016 from the Japanese Patent Office in counterpart application No. 2014-176911.

*Primary Examiner* — Shefali Goradia
(74) *Attorney, Agent, or Firm* — Sughrue Mion, PLLC

(57) ABSTRACT

A medical image measuring apparatus includes a tissue information label assigning unit that assigns each point of a medical image with a tissue information label representing tissue information each point belongs, a measuring unit that performs measurement in the medical image, and a measurement subject label assigning unit that determines, based on a tissue information label assigned to a measurement point or a point within a region of interest used for the measurement, a measurement subject label representing a measurement subject and assigns the label to a result of the measurement.

10 Claims, 5 Drawing Sheets

| MEASUREMENT POINT | TUMOR (CENTER) | TUMOR (PERIPHERY) | TUMOR (OTHERS) | ARTERY (WALL) | ARTERY (CENTER LINE) | ARTERY (OTHERS) | ... |
|---|---|---|---|---|---|---|---|
| TUMOR (CENTER) | N/A | TUMOR RADIUS | DISTANCE | DISTANCE BETWEEN TUMOR AND ARTERY | DISTANCE BETWEEN TUMOR AND ARTERY | DISTANCE BETWEEN TUMOR AND ARTERY | |
| TUMOR (PERIPHERY) | TUMOR RADIUS | TUMOR DIAMETER | TUMOR DIAMETER | DISTANCE BETWEEN TUMOR AND ARTERY | DISTANCE BETWEEN TUMOR AND ARTERY | DISTANCE BETWEEN TUMOR AND ARTERY | |
| TUMOR (OTHERS) | DISTANCE | DISTANCE | DISTANCE | DISTANCE BETWEEN TUMOR AND ARTERY | DISTANCE BETWEEN TUMOR AND ARTERY | DISTANCE BETWEEN TUMOR AND ARTERY | |
| ARTERY (WALL) | DISTANCE BETWEEN ARTERY AND TUMOR | DISTANCE BETWEEN ARTERY AND TUMOR | DISTANCE BETWEEN ARTERY AND TUMOR | ARTERY DIAMETER | ARTERY RADIUS | DISTANCE | |
| ARTERY (CENTER LINE) | DISTANCE BETWEEN ARTERY AND TUMOR | DISTANCE BETWEEN ARTERY AND TUMOR | DISTANCE BETWEEN ARTERY AND TUMOR | ARTERY RADIUS | N/A | DISTANCE | |
| ARTERY (OTHERS) | DISTANCE BETWEEN ARTERY AND TUMOR | DISTANCE BETWEEN ARTERY AND TUMOR | DISTANCE BETWEEN ARTERY AND TUMOR | DISTANCE | DISTANCE | DISTANCE | |
| : | | | | | | | |
| : | | | | | | | |

(51) Int. Cl.
    *A61B 5/107*     (2006.01)
    *G06T 7/00*     (2017.01)
    *A61B 6/03*     (2006.01)
    *A61B 6/00*     (2006.01)
    *A61B 5/00*     (2006.01)
    *G01R 33/56*     (2006.01)
    *G06F 19/00*     (2018.01)

(56) References Cited

U.S. PATENT DOCUMENTS

| | | | |
|---|---|---|---|
| 9,390,533 B2 * | 7/2016 | Yoo | G06T 7/60 |
| 2011/0282206 A1 | 11/2011 | Ichioka et al. | |
| 2013/0162805 A1 * | 6/2013 | Takayama | G06T 11/60 |
| | | | 348/80 |
| 2014/0236010 A1 | 8/2014 | Nakano | |
| 2015/0187118 A1 | 7/2015 | Masumoto | |
| 2015/0220240 A1 * | 8/2015 | Tsukijishin | A61B 5/7445 |
| | | | 348/77 |

FOREIGN PATENT DOCUMENTS

| | | |
|---|---|---|
| JP | 2006-34337 A | 2/2006 |
| JP | 2008-142532 A | 6/2008 |
| JP | 2008-212508 A | 9/2008 |
| JP | 2010-194007 A | 9/2010 |
| JP | 2011-255165 A | 12/2011 |
| JP | 2013-134744 A | 7/2013 |
| JP | 2014-54428 A | 3/2014 |
| JP | 2014-64708 A | 4/2014 |
| WO | 2014/034294 A1 | 3/2014 |

* cited by examiner

FIG.2

| MEASUREMENT POINT | TUMOR (CENTER) | TUMOR (PERIPHERY) | TUMOR (OTHERS) | ARTERY (WALL) | ARTERY (CENTER LINE) | ARTERY (OTHERS) | ... |
|---|---|---|---|---|---|---|---|
| TUMOR (CENTER) | N/A | TUMOR RADIUS | DISTANCE | DISTANCE BETWEEN TUMOR AND ARTERY | DISTANCE BETWEEN TUMOR AND ARTERY | DISTANCE BETWEEN TUMOR AND ARTERY | |
| TUMOR (PERIPHERY) | TUMOR RADIUS | TUMOR DIAMETER | TUMOR DIAMETER | DISTANCE BETWEEN TUMOR AND ARTERY | DISTANCE BETWEEN TUMOR AND ARTERY | DISTANCE BETWEEN TUMOR AND ARTERY | |
| TUMOR (OTHERS) | DISTANCE | DISTANCE | DISTANCE | DISTANCE BETWEEN TUMOR AND ARTERY | DISTANCE BETWEEN TUMOR AND ARTERY | DISTANCE BETWEEN TUMOR AND ARTERY | |
| ARTERY (WALL) | DISTANCE BETWEEN ARTERY AND TUMOR | DISTANCE BETWEEN ARTERY AND TUMOR | DISTANCE BETWEEN ARTERY AND TUMOR | ARTERY DIAMETER | ARTERY RADIUS | DISTANCE | |
| ARTERY (CENTER LINE) | DISTANCE BETWEEN ARTERY AND TUMOR | DISTANCE BETWEEN ARTERY AND TUMOR | DISTANCE BETWEEN ARTERY AND TUMOR | ARTERY RADIUS | N/A | DISTANCE | |
| ARTERY (OTHERS) | DISTANCE BETWEEN ARTERY AND TUMOR | DISTANCE BETWEEN ARTERY AND TUMOR | DISTANCE BETWEEN ARTERY AND TUMOR | DISTANCE | DISTANCE | DISTANCE | |
| ... | | | | | | | |

MEDICAL IMAGE MEASURING APPARATUS, METHOD, AND MEDIUM

CROSS-REFERENCE TO RELATED APPLICATIONS

The present application claims priority under 35 U.S.C. § 119 to Japanese Patent Application No. 2014-176911 filed on Sep. 1, 2014. The above application is hereby expressly incorporated by reference, in its entirety, into the present application.

BACKGROUND OF THE INVENTION

Field of the Invention

The present invention relates to a medical image measuring apparatus, method, and program that performs measurement in a medical image based on a specified measurement point.

Description of the Related Art

Heretofore, it has been practiced to measure a given characteristic amount of a target of attention, such as an organ or a lesion, included in a medical image, such as a radiation image, a magnetic resonance imaging (MRI) image, an ultrasound image, or the like, and to confirm the presence or absence of an abnormality in the organ or the growth of the lesion based on a result of the measurement.

For example, Japanese Unexamined Patent Publication No. 2014-064708 proposes that information of measurement site and item is add to a result of measurement performed based on an ultrasound image and this information is used in generating a diagnosis report. Japanese Unexamined Patent Publication No. 2011-255165 proposes that a menu of measurement items is displayed when measurement is performed using an ultrasound image. Japanese Unexamined Patent Publication No. 2010-194007 proposes that brightness or velocity within a region of interest in an ultrasound image is measured, and a result of the measurement and the name of the site of the region of interest are displayed. Japanese Unexamined Patent Publication No. 2008-142532 proposes that a doctor's comment is added to a result of measurement performed using of a medical image. Further, Japanese Unexamined Patent Publication No. 2000-185038, Japanese Unexamined Patent Publication No. 2008-212508, and Japanese Unexamined Patent Publication No. 9 (1997)-251364 propose that a measurement result and a measurement item are displayed.

SUMMARY OF THE INVENTION

Here, as described above, it has been conventionally practiced to perform measurement using a medical image and to display a result of the measurement and a measurement item, but it has been necessary that the measurement item is set and inputted by the user, causing a problem of troublesome work for that.

In view of the circumstances described above, it is an object of the present invention to provide a medical image measuring apparatus, method, and program capable of automatically assigning a measurement subject label to a result of measurement performed in a medical image, without being manually set and inputted by the user.

A medical image measuring apparatus of the present invention includes a tissue information label assigning unit that assigns each point of a medical image with a tissue information label representing tissue information each point belongs, a measuring unit that performs measurement in the medical image, and a measurement subject label assigning unit that determines, based on a tissue information label assigned to a measurement point or a point within a region of interest used for the measurement, a measurement subject label representing a measurement subject and assigns the label to a result of the measurement.

In the foregoing medical image measuring apparatus of the present invention, the measuring unit may perform distance measurement using the measurement point.

Further, the measuring unit may perform angle measurement using the measurement point.

Still further, the measuring unit may perform characteristic amount measurement of the region of interest.

Further, the measurement subject label assigning unit may further receive an input of a measurement item of the measurement and determine the measurement subject label based on the measurement item and the tissue information label assigned to the measurement point or the point in the region of interest.

Still further, the tissue information label may represent a tumor, a blood vessel, or an organ.

Further, the tissue information label may represent a tumor center, a tumor periphery, a blood vessel center, a blood vessel wall, an organ center, or an organ periphery.

Still further, the measurement subject label assigning unit may include a table associating the tissue information label with the measurement subject label and determine the measurement subject label using the table.

Further, the measurement subject label assigning unit may receive a comment input and assign the comment to the result of the measurement.

A medical image measuring method of the present invention includes the steps of assigning each point of a medical image with a tissue information label representing tissue information each point belongs, performing measurement in the medical image, and determining, based on a tissue information label assigned to a measurement point or a point within a region of interest used for the measurement, a measurement subject label representing a measurement subject and assigning the label to a result of the measurement.

A medical image measuring program of the present invention causes a computer to function as a tissue information label assigning unit that assigns each point of a medical image with a tissue information label representing tissue information each point belongs, a measuring unit that performs measurement in the medical image, and a measurement subject label assigning unit that determines, based on a tissue information label assigned to a measurement point or a point within a region of interest used for the measurement, a measurement subject label representing a measurement subject and assigns the label to a result of the measurement.

According to the medical image measuring apparatus, method, and program of the present invention, each point of a medical image is assigned with a tissue information label representing tissue information each point belongs and, based on a tissue information label assigned to a measurement point or a point within a region of interest used for the measurement, a measurement subject label representing a measurement subject is determined and assigned to a result of the measurement. This allows the measurement subject label to be automatically assigned to the result of the measurement without being manually set and inputted by the user.

BRIEF DESCRIPTION OF THE DRAWINGS

FIG. 2 shows an example of a table associating tissue information labels with measurement subject labels.

DETAILED DESCRIPTION OF THE PREFERRED EMBODIMENTS

Figure 1:
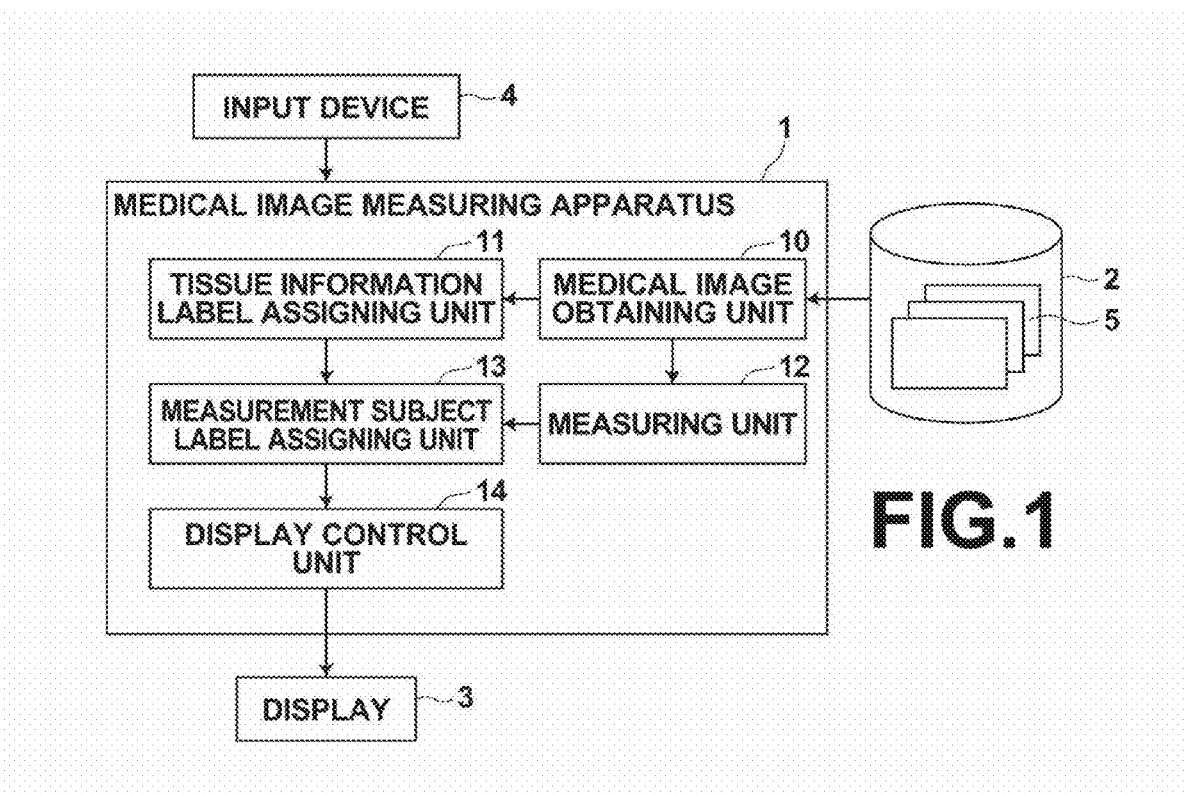
FIG. 1 is a block diagram of a medical image diagnosis support system that uses an embodiment of the medical image measuring apparatus, method, and program, illustrating a schematic configuration thereof.

Hereinafter, a medical image diagnosis support system that uses an embodiment of the medical image measuring apparatus, method, and program of the present invention will be described with reference to the accompanying drawings. FIG. 1 is a block diagram of the medical image diagnosis support system of the present embodiment, illustrating a schematic configuration thereof.

As illustrated in FIG. 1, the medical image diagnosis support system of the present embodiment includes a medical image measuring apparatus 1, a medical image storage server 2, a display 3, and an input device 4.

The medical image measuring apparatus 1 is configured by installing a medical image measuring program of the present embodiment on a computer.

The medical image measuring apparatus 1 includes a central processing unit (CPU) and storage devices, such as a semiconductor memory, a hard disk, and a solid state drive (SSD). The storage device includes the medical image measuring program of the present embodiment, and execution of the medical image measuring program by the central processing unit causes the operation of a medical image obtaining unit 10, a tissue information label assigning unit 11, a measuring unit 12, a measurement subject label assigning unit 13, and display control unit 14 shown in FIG. 1.

The medical image obtaining unit 10 obtains a medical image 5 of a patient captured in advance. The medical image 5 may be, for example, a tomographic image captured by a computed tomography (CT) system, a magnetic resonance imaging (MRI) system, or the like, or a three-dimensional image composed of a plurality of tomographic images. The tomographic images may include axial cross-sectional images, sagittal cross-sectional images, coronal cross-sectional images, and other multi-planar reconstruction (MPR) cross-sectional images.

The medical image 5 is stored in the medical image storage server 2 in advance with patient identification information and, based on patient identification information inputted by the user using the input device 4, the medical image obtaining unit 10 reads out a medical image 5 having the patient identification information from the medical image storage server 2.

The tissue information label assigning unit 11 assigns each point (pixel or voxel) of a medical image with a tissue information label representing tissue information each point belongs. The tissue information label represents tissue information, such as a blood vessel, a bronchus, an organ, like heart or liver, or a lesion, like tumor or calcification.

The tissue information label may also include the position information of the point to which the tissue information label is assigned in an organ or in a lesion. More specifically, for example, a tissue information label that includes information representing a tumor and information representing a tumor center may be assigned to a point located in the center of a tumor included in a medical image. Example position information may include, other than the tumor center, a tumor periphery, a tumor position other than the center and the periphery, an artery wall, an artery center line, an artery position other than the artery wall and the artery center line, but the position information is not limited to these and information of other positions may be included in the tissue information label.

The tissue information label may be automatically determined based on the medical image and assigned to each point by the tissue information label assigning unit 11, or tissue label information may be manually inputted by the user using the input device 4 and the inputted tissue label information may be assigned to each point in the medical image by the tissue information label assigning unit 11.

In the case where the tissue information is automatically assigned by the tissue information label assigning unit 11, the tissue information label assigning unit 11 automatically extracts a blood vessel, a bronchus, an organ such as a liver, and a lesion from a medical image. In that case, any known extraction method may be used.

The position of a point assigned with a tissue information label may be obtained by performing measurement based on an image of an extracted organ or a lesion and determining whether the point is located in the center or in the periphery of the organ or the lesion.

The position of a point in an organ or lesion may be measured when each point is assigned with a tissue information label, or otherwise, after a measurement point, to be described in detail later, is specified in a medical image by the user, the position in the organ or lesion at the specified measurement point may be measured.

The position information, such as the center or periphery, may not be precise and, for example, the position information representing the center or center line may be assigned to a point located within a predetermined adjacent range from the center or center line of an organ or a lesion, while the position information representing the periphery may be assigned to a point located within a predetermined adjacent range from the edge of an organ or a lesion. Further, the position information of the tissue information label may be obtained using the center point or center line information used when extracting the organ or lesion from the medical image.

The measuring unit 12 performs measurement in a medical image. More specifically, for example, two or three measurement points or a region of interest is specified in a medical image displayed on the display 3 by the user using the input device 4 and the measuring unit 12 performs measurement for a predetermined measurement item based on the specified measurement points or the region of interest. Example measurement items include a distance measured by two measurement points, an angle measured by three measurement points, and a characteristic amount measured based on an image in the region of interest. Examples of characteristic amounts of the region of interest include an average value, a maximum value, or a minimum value of density within the region of interest, and an area, a contour length, or a long axis length of an organ or a lesion included in the region of interest. The "measurement in a medical image" refers to measurement of; for example, a distance, an angle, and an area, as described above, but the measurement items are not limited to these.

The measurement subject medical image may be a three-dimensional image or a two-dimensional image, such as a tomographic image. In the case of measurement of a three-dimensional image, the measurement may be performed in the three-dimensional space or in the two-dimensional space which is a two-dimensional screen onto which the three-dimensional image is projected.

The measurement subject label assigning unit 13 determines, based on a tissue information label assigned to a measurement point or a point in a region of interest used for the measurement in the measuring unit 12, a measurement subject label representing a measurement subject and assigns the label to a result of the measurement. The measurement subject label is a label that indicates a measurement subject. Example measurement subject labels include those constituted by a measurement subject tissue name and a measured place name, such as "TUMOR RADIUS" and "ARTERY DIAMETER", those constituted by a measurement subject tissue name and a measurement item name, such as "DISTANCE BETWEEN TUMOR AND ARTERY", and those constituted only by a measurement item name, such as "DISTANCE", "AVERAGE DENSITY". Note that the measurement subject labels are not limited to those described above, and any label may be used as long as it represents a measurement subject.

More specifically, the measurement subject label assigning unit 13 of the present embodiment is provided with a table as shown in FIG. 2 and determines the measurement subject label with reference to the table. The table shown in FIG. 2 is a table used for distance measurement, and the top row in the table indicates tissue information labels for one measurement point used for distance measurement, while the left most column in the table indicates tissue information labels for the other measurement point used for distance measurement.

In the table shown in FIG. 2, "TUMOR (CENTER)" is a tissue information label to be assigned to a point near a tumor center, "TUMOR (PERIPHERY)", is a tissue information label to be assigned to a point near a tumor periphery, and "TUMOR (OTHERS)" is a tissue information label to be assigned to a point located at a place other than near the tumor center and near the tumor periphery. Further, "ARTERY (WALL)" is a tissue information label to be assigned to a point near an artery boundary, "ARTERY (CENTER LINE)" is a tissue information label to be assigned to a point near an artery center line, and "ARTERY (OTHERS)" is a tissue information label to be assigned to a point located at a place other than near the artery boundary and near the artery center line.

Then, for example, the tissue information labels of the two measurement points specified by the user are "ARTERY (OTHERS)" and "TUMOR (OTHERS)" as indicated by thick frames in the table of FIG. 2, the measurement subject label assigning unit 13 determines "DISTANCE BETWEEN TUMOR AND ARTERY" as the measurement subject label. In this way, the measurement subject label assigning unit 13 determines the measurement subject label based on the tissue information labels of the measurement points.

As described above, the table shown in FIG. 2 is used for measuring a distance between two measurement points. In a case, for example, where an angle is measured by specifying three points as the measurement points, an angle measurement table may be used and a measurement subject label may be determined based on tissue information labels of the three measurement points.

Figure 3:
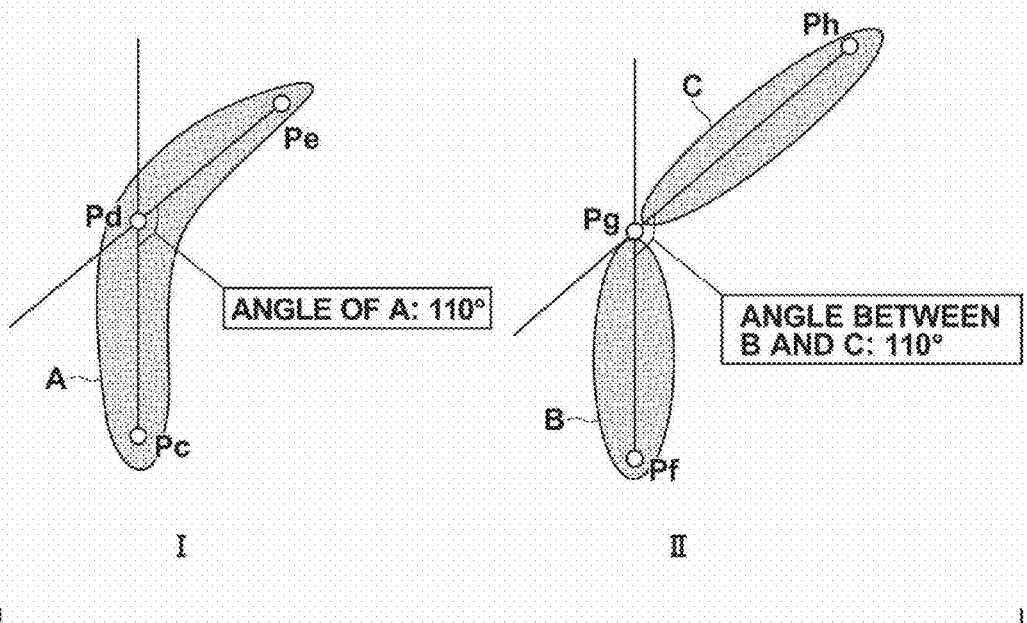
FIG. 3 is a drawing for explaining a measurement subject label determination method in a case of angle measurement.

Here, a measurement subject label may be determined when performing angle measurement by a method in which if, for example, three measurement points Pc, Pd, and Pe are all included in a region of a measurement subject A, as shown in I of FIG. 3, "ANGLE OF A" is determined as the measurement subject label, while if a first measurement point Pf is included in a region of a measurement subject B, a second measurement point Ph is included in a region of a measurement subject C, and a third measurement point Pg lies between the measurement subject B and the measurement subject C, and included neither in the measurement subject B nor in the measurement subject C, as shown in II of FIG. 3, "ANGLE BETWEEN B AND C" is determined as the measurement subject label.

Figure 4:
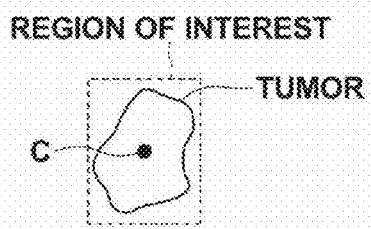
FIG. 4 is a drawing for explaining a measurement subject label determination method in a case of characteristic amount measurement of a region of interest.

Further, a measurement subject label may be determined when performing characteristic amount measurement of a region of interest by a method in which if, for example, a region of interest is specified to enclose a tumor mass, as illustrated in FIG. 4, a tissue information label of the center point C of the region of interest is obtained and a measurement subject label, such as "TUMOR MASS AREA", "TUMOR MASS AVERAGE DENSITY", or the like, is determined based on the tissue information label.

Further, the measurement items, such as a distance between two points, an angle, an area of a region of interest, and an average density of a region of interest, may be set and inputted by the user using the input device 4. Then a measurement subject label may be determined based on a measurement item and a tissue information label set and inputted by the user.

More specifically, if the distance between two points is set and inputted by the user as the measurement item, the measurement subject label may be determined using the table as shown in FIG. 2, if the angle is set and inputted as the measurement item, the measurement subject label may be determined using the angle measurement table, if the area of a region of interest is set and inputted as the measurement item, a combination of the name of the organ or lesion in the region of interest and "AREA" may be determined as the measurement subject label (e g., "TUMOR AREA"), and if the average density of the region of interest is set and inputted as the measurement item, a combination of the name of the organ or lesion in the region of interest and "AVERAGE DENSITY" may be determined as the measurement subject label (e.g., "TUMOR AVERAGE DENSITY").

Further, a curvature degree may be set as a measurement item, and in a case where the curvature degree is set and inputted by the user and three points of a spine are specified, a curvature degree may be measured based on the three points and "SPINE CURVATURE DEGREE" may be determined as the measurement subject label.

In a case where measurement is performed in a two-dimensional space which is a two dimensional screen onto which a three-dimensional image is projected, if, for example, a measurement point is specified within a tumor, the discrimination cannot be made whether the measurement point is in the tumor center or in the tumor periphery, since a depth direction cannot be specified in the two-dimensional space. Therefore, in such a case, the specified measurement point may be simply recognized as a measurement point on a tumor and a measurement subject label, such as "DISTANCE BETWEEN TUMOR AND ARTERY" may be assigned. Note that it is possible to discriminate between a center point and a peripheral point on a tomographic image and, for example, the center and periphery of a tumor may be specified as measurement points, whereby a measurement subject label, such as "TUMOR RADIUS" may be determined and assigned based on the tissue information labels of these measurement points.

The display control unit 14 displays a medical image obtained by the medical image obtaining unit 10 and a result of the measurement in the measuring unit 12 on the display 3. The display control unit 14 of the present embodiment, in particular, displays a measurement subject label assigned to a result of the measurement in the measurement subject label assigning unit 13 near the result of the measurement.

The input device 4 receives various setting inputs by the user and is constituted by a keyboard and a mouse. The input device 4 of the present embodiment is capable of receiving a setting input of a measurement point or a region of interest, and a setting input of a tissue information label, as described above.

Figure 5:
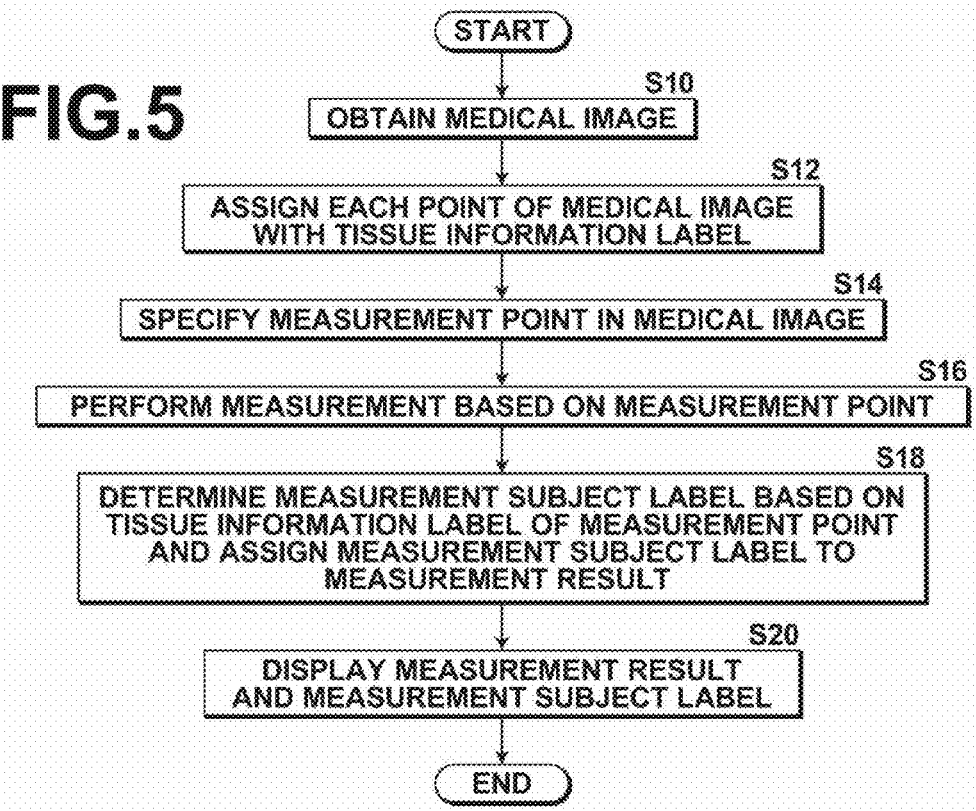
FIG. 5 is a flowchart for explaining an operation of the medical image diagnosis support system that uses an embodiment of the medical image measuring apparatus, method, and program of the present invention.

Next, an operation of the medical image diagnosis support system of the present embodiment will be described with reference to a flowchart shown in FIG. 5. Here, a description will be made of a case in which two measurement points are specified and distance measurement is performed.

First, a medical image is read out and obtained from the medical image storage server 2 by the medical image obtaining unit 10 based on an input of patient identification information or the like by the user (S10).

The medical image obtained by the medical image obtaining unit 10 is outputted to the tissue information label assigning unit 11 and the measuring unit 12. Then, each point of the medical image is assigned with a tissue information label in the tissue information assigning unit 11 (S12).

Figure 6:
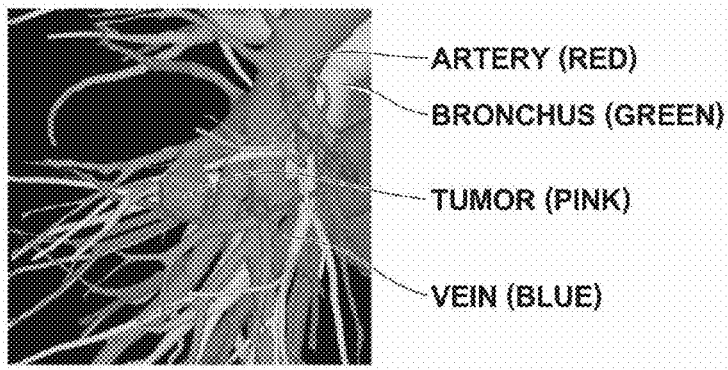
FIG. 6 shows a display example of a medical image with assigned tissue information labels.

The tissue information labels are outputted to the display control unit 14, and the display control unit 14 allocates a different color to each tissue information label and displays on the display 3. FIG. 6 shows an example in which tissue information labels are assigned to a bronchus, an artery, a vein, and a tumor in a medical image respectively and displayed by allocating a green color to the tissue information label of the bronchus, a red color to the tissue information label of the artery, a blue color to the tissue information label of the vein, and a pink color to the tissue information label of the tumor.

Figure 7:
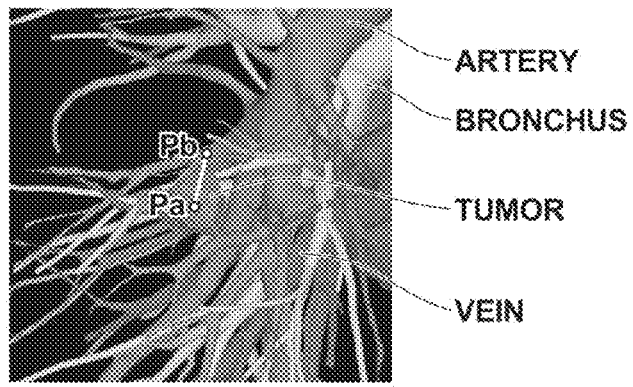
FIG. 7 shows an example of a measurement point specified in a medical image.

Then, in the medical image like that shown in FIG. 6, measurement points are specified by the user (S14). FIG. 7 shows an example in which one measurement point Pa is specified on a tumor, while another measurement point Pb is specified on an artery when distance measurement is performed in the medical image.

When the measurement points are specified by the user, the measuring unit 12 performs measurement based on the specified measurement points (S16). More specifically, when the measurement point Pa and the measurement point Pb are specified, as shown in FIG. 7, the measuring unit 12 measures the distance between the measurement point Pa and the measurement point Pb and outputs a result of the measurement to the measurement subject label assigning unit 13.

In the meantime, when the measurement points are specified by the user, the tissue information labels of the measurement points are outputted to the measurement subject label assigning unit 13, and the measurement subject label assigning unit 13 determines a measurement subject label based on the inputted tissue information labels as described above. Then, the measurement subject label assigning unit 13 assigns the measurement subject label to a result of the measurement outputted from the measuring unit 12 (S18) and outputs to the display control unit 14.

Figure 8:
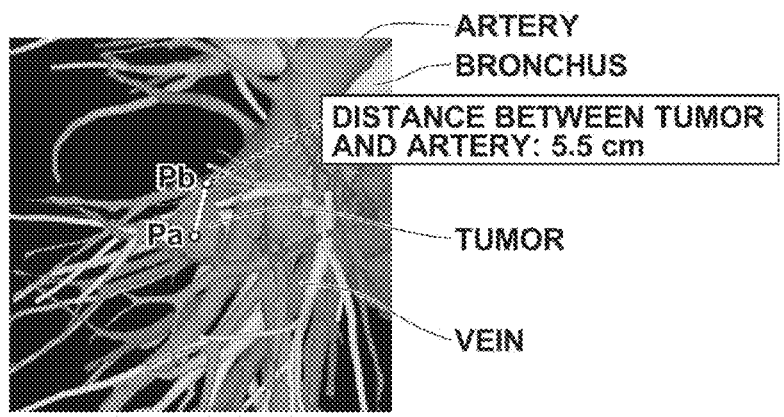
FIG. 8 shows a display example of a measurement subject label.
Figure 9:
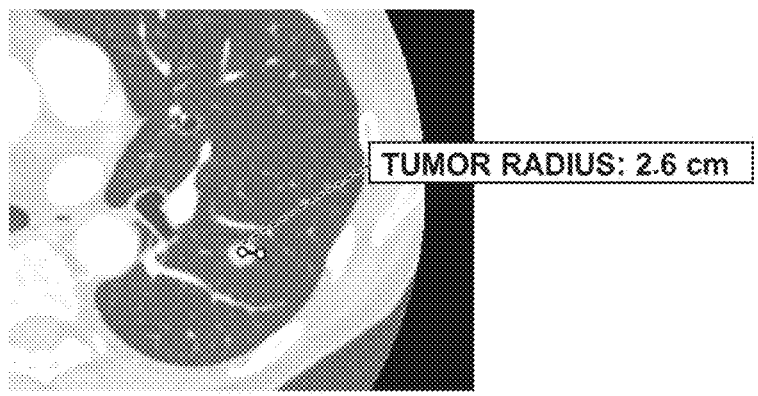
FIG. 9 shows another display example of a measurement subject label.

The display control unit 14 displays the inputted measurement result and the measurement subject label on the display 3 (S20). FIG. 8 shows an example in which the measurement result "5.5 cm" of the distance between the measurement point Pa and the measurement point Pb and the measurement subject label "DISTANCE BETWEEN TUMOR AND ARTERY" are displayed. FIG. 9 shows an example in which, in a case where the center and periphery of a tumor are specified as the measurement points, the measurement result "2.6 cm" and the measurement subject label "TUMOR RADIUS" are displayed.

When displayed by the display control unit 14, the measurement result and the measurement subject label are preferably displayed near the measurement subject. Further, it is preferable that the relationship between the measurement subject and the measurement subject label with the measurement result can be understood instantly by tying the measurement subject and the measurement result with the measurement subject label by a dotted line or a solid line, as illustrated in FIGS. 8 and 9, or displaying an arrow from the measurement result with the measurement subject label toward the measurement subject. But, the display methods are not limited to these and, for example, the measurement result with the measurement subject label may be displayed on a display different from the display 3 on which that medical image is displayed.

According to the medical image diagnosis support system of the foregoing embodiment, each point of a medical image is assigned with a tissue information label representing tissue information each point belongs. Then, based on a tissue information label assigned to a measurement point or a point within a region of interest, a measurement subject label is determined and assigned to a result of the measurement. This allows the measurement subject label to be assigned automatically by requiring the user only to specify a measurement point or a region of interest.

Further, a comment set and inputted by the user using the input device 4 may be received by the measurement subject label assigning unit 13 to assign the comment to a measurement result and displayed on the display 3. This allows a doctor's comment or the like to be assigned to the measurement result.

Still further, in the foregoing embodiment, a measurement subject label and a comment are assigned to a measurement result and displayed, but these may be not only displayed but also automatically written, for example, in a diagnostic report generated on a computer.

What is claimed is:

1. A medical image measuring apparatus, comprising:
   a memory; and
   a processor coupled to the memory and the processor configured to:
   assign each point of a medical image with a tissue information label representing tissue information to which the each point belongs;
   perform measurement in the medical image; and
   determine, based on a tissue information label assigned to a measurement point or a point within a region of interest used for the measurement, a measurement subject label representing a measurement subject and assigns the measurement subject label to a result of the measurement, wherein the measurement subject label comprises a measurement subject tissue name and a measured place name, or a measurement subject tissue name and a measurement item name, or a measurement item name, and wherein the memory stores a table associating the tissue information label with the measurement subject label and wherein, based on a first tissue information label of a first measurement point and a second tissue information label of a second measurement label, the processor determines the measurement subject label using the table.

2. The medical image measuring apparatus of claim 1, wherein the processor performs distance measurement using the measurement point.

3. The medical image measuring apparatus of claim 1, wherein the processor performs angle measurement using the measurement point.

4. The medical image measuring apparatus of claim 1, wherein the processor performs characteristic amount measurement of the region of interest.

5. The medical image measuring apparatus of claim 1, wherein the processor further receives an input of a measurement item of the measurement and determines the measurement subject label based on the measurement item and the tissue information label assigned to the measurement point or the point in the region of interest.

6. The medical image measuring apparatus of claim 1, wherein the tissue information label represents a tumor, a blood vessel, or an organ.

7. The medical image measuring apparatus of claim 1, wherein the tissue information label represents a tumor center, a tumor periphery, a blood vessel center, a blood vessel wall, an organ center, or an organ periphery.

8. The medical image measuring apparatus of claim 1, wherein the processor receives a comment input and assigns the comment to the result of the measurement.

9. A medical image measuring method comprising:

assigning each point of a medical image with a tissue information label representing tissue information to which the each point belongs;

performing measurement in the medical image;

determining, based on a tissue information label assigned to a measurement point or a point within a region of interest used for the measurement, a measurement subject label representing a measurement subject and assigning the measurement subject label to a result of the measurement; and storing a table in which the tissue information label is associated with the measurement subject label, wherein the measurement subject label comprises a measurement subject tissue name and a measured place name, a measurement subject tissue name and a measurement item name, or a measurement item name, and wherein, based on a first tissue information label of a first measurement point and a second tissue information label of a second measurement label, measurement subject label is determined using the table.

10. A non-transitory computer-readable recording medium containing a medical image measuring program that causes a computer to execute the following operations:

assign each point of a medical image with a tissue information label representing tissue information to which the each point belongs;

perform measurement in the medical image;

determine, based on a tissue information label assigned to a measurement point or a point within a region of interest used for the measurement, a measurement subject label representing a measurement subject and assigns the measurement subject label to a result of the measurement; and store a table in which the tissue information label is associated with the measurement subject label, wherein the measurement subject label comprises a measurement subject tissue name and a measured place name, a measurement subject tissue name and a measurement item name, or a measurement item name, and wherein, based on a first tissue information label of a first measurement point and a second tissue information label of a second measurement label, measurement subject label is determined using the table.

* * * * *